United States Patent [19]

Brenneman et al.

[11] Patent Number: 5,767,240
[45] Date of Patent: Jun. 16, 1998

[54] ACTIVITY-DEPENDENT NEUROTROPHIC FACTOR

[75] Inventors: Douglas E. Brenneman, Damascus, Md.; Illana Gozes, Tel Aviv, Israel

[73] Assignee: The United States of America as represented by the Department of Health and Human Services, Washington, D.C.

[21] Appl. No.: 871,973

[22] Filed: Apr. 22, 1992

Related U.S. Application Data

[63] Continuation-in-part of Ser. No. 688,087, Apr. 22, 1991, abandoned.

[51] Int. Cl.$^6$ .......................... C07K 14/475; C07K 16/22; C07K 1/00; C07K 1/14
[52] U.S. Cl. ............. 530/350; 530/388.24; 530/388.9; 530/389.2; 530/412; 530/416; 530/413; 530/417; 530/399; 530/395; 530/388.23; 530/839; 530/300; 435/41
[58] Field of Search ........................ 514/21; 424/85.8, 424/139.1, 145.1, 158.1; 435/41; 530/300, 839, 388.23, 350, 388.24, 388.9, 389.2, 389.8, 412, 416, 413, 417, 399, 395

[56] References Cited

FOREIGN PATENT DOCUMENTS

WO 90/10449  9/1990  WIPO .
WO 92/18140  10/1992  WIPO .
WO 94/03208  2/1994  WIPO .

OTHER PUBLICATIONS

Brenneman et al., Soc. for Neurosci Abstracts, 17: 754, 1991.
Webster's II New Riverside Dictionary, The Riverside Publishing Co., 1988, p. 1016.
Branch et al., J. Immunol. Methods, 143(2):251–261, 1991 (Abstract thereof).
Wahl et al., J. Immunol. 140(9):3026–32, 1988, (Abstract thereof).
Hall et al., J. Cell Physiol., 141 (1): 154–9, 1989, (Abstract thereof).
Fahey et al., Clin Exp. Immunol. 88: 1–5, 1992.
Fathman et al., Ann. Rev. Immunol. 1, 633–55, 1983.
Brenneman et al. (1987), J. Cell Biol., vol. 104, pp. 1603–1610.
Brenneman et al. (1988), Nature, vol. 335, pp. 632–649.
Waldman (1991), Science vol. 252, pp. 1657–1662.
Goding, Monoclonal Antibodies: Principles and Practice, Chapters 3, pp. 59–93 Academic Press 1986.
Goding, Monoclonal Antibodies: Ratio Principles and practices: Chapter 8, pp. 281–293 Academic Press, 1986.

*Primary Examiner*—Ronald B. Schwadron
*Attorney, Agent, or Firm*—Townsend and Townsend and Crew LLP

[57] ABSTRACT

The present invention relates to a purified non-neuronal activity-dependent neurotrophic factor (ADNF) protein that increase the survival of spinal cord neuron cells, cerebral cortical cells and hippocampal neuron cells which has a molecular weight of 16,000 to 18,000 Daltons as determined by sodium dodecyl sulfate polyacrylamide gel electrophoresis, and a basic pI of about 8.1.

10 Claims, 12 Drawing Sheets

SUMMARY

| STEP | PROTEIN | UNITS | SPECIFIC ACTIVITY |
|---|---|---|---|
| 1. TOTAL | 5400 ug | 43 MILLION | 8 U/ng |
| 2. DEAE | 467 ug | 41.5 MILLION | 89 U/ng |
| 3. SIZING | 5 ug | 5.5 MILLION | 1100 U/ng |
| 4. REVERSE PHASE | 0.28 ug | 3.7 MILLION | 13,200 U/ng |

YIELD: 0.005%
PURIFICATION: 1650 X

*FIG. 6.*

ACTIVITY-DEPENDENT NEUROTROPHIC FACTOR

The subject patent application is a continuation-in-part of Ser. No. 07/688,087, filed Apr. 22, 1991, now abandoned.

BACKGROUND OF THE INVENTION

1. Field of the Invention

The present invention relates to activity-dependent neurotrophic factors (ADNF). In particular, the present invention relates to purified non-neuronal ADNF and uses thereof for the treatment of neurological deficiencies and for the prevention of AIDS related neuronal cell death, or dystrophy.

2. Background Information

Neuronal maturation and survival are dependent on protein growth factors during development. The present inventors have sought to isolate a novel growth factor that increases the survival of activity-dependent spinal cord neurons. These neurons are activity-dependent in the sense that their survival is also influenced by electrical activity (Brenneman et al., (1985) J. Pharmacol. Exp. Therap. 233, 402–408; Brenneman et al., (1983) Dev. Brain Res. 9, 13–27;and Brenneman et al., (1984) Dev. Brain Res. 15, 211–217). Previous studies carried out by the present inventors have indicated that a part of the molecular basis of this activity-dependence is the action of vasoactive intestinal peptide (VIP), a neuropeptide which is released during electrical activity (Brenneman D. E. and Eiden L. E. (1986) Proc. Natl. Acad Sci. U.S.A 83, 1159–1162; and Brenneman et al., (1985) Peptides 6 (suppl. 2) 35–39). Previous work also indicated that VIP increased the survival of activity-dependent spinal cord neurons by releasing a protein growth factor from non-neuronal spinal cord cells (Brenneman et al., (1987) J. Cell Biology. 104, 1603–1610). The working hypothesis supported by the present invention is that VIP interacts with its receptors on glial cells (Gozes et al., (1989) Soc. Neurosci. Abs. 15, 216) to induce the secretion of neuronal survival factor(s) (Brenneman et al., (1990) J. Neurosci. Res. 25, 386–394; and Gozes, I. and Brenneman, D. E. (1989) Molecular Neurobiology, 3, 201–236).

Previously, growth factors such as NGF (Levi-Montalcini, R. and Angeletti, P. V. (1968) Physiol. Rev. 48, 534–569), CNTF (Lin et al., (1989) Science 246, 1023–1025), FGF (Walicke et al., (1986) Proc. Natl. Acad. Sci. USA 83, 3012–3016) and BDNF (Leibrock et al., (1989) Nature 341, 149–152) have been isolated and shown to provide neurotrophic support for specific populations of neurons. The growth factor of the present invention (ADNF) differs from all other known growth factors on the basis of: 1) specificity of the target population of neurons; 2) structural characteristics of the protein, such as, total amino acid composition, and chromatographic properties; and 3) relationship to vasoactive intestinal peptide and electrical activity.

SUMMARY OF THE INVENTION

It is an object of the present invention to provide a purified ADNF protein. The purified protein of the present invention increases the survival of activity-dependent spinal cord neurons and cerebral cortical neurons and prevents neuronal cell death resulting from HIV infection.

Various other objects and advantages of the present invention will become apparent from the following description of the invention and the drawings.

In one embodiment, the present invention relates to a purified non-neuronal activity-dependent neurotrophic factor (ADNF) protein that increases the survival of neuron cells which has molecular weight of 16,000 to 18,000 Daltons or fragments thereof comprising at least 6 amino acids each. The present invention further relates to antibodies, monoclonal and polyclonal, specific for the ADNF protein or fragment thereof.

In another embodiment, the present invention relates to a pharmaceutical composition for protection against neuronal cell death comprising the purified ADNF protein of the present invention or a fragment of the proteins, in an amount sufficient to protect the neuronal cells and a pharmaceutically acceptable carrier.

In a further embodiment, the present invention relates to methods of treating neurological deficiencies and methods of preventing neuronal cell death in a patient infected with human immunodeficiency virus involving administration of the ADNF protein or a fragment thereof to patients.

BRIEF DESCRIPTION OF THE DRAWINGS

FIG. 6 is a summary of the purification scheme of ADNF, showing the starting material, its total biological activity and the specific activity of the neuronal survival factor. The increase in specific activity is shown for each purification step. Starting from the original secreted proteins, a 1650-fold purification was achieved to apparent homogeneity.

DETAILED DESCRIPTION OF THE PREFERRED EMBODIMENT

The present invention relates to a purified glial-derived, VIP-released growth factor protein. Using a combination of ion exchange chromatography, molecular sieving technologies employing FPLC, reverse phase chromatography, polyacrylamide gel electrophoresis, isoelectric focusing and microsequencing, the present inventors have identified and isolated a VIP-releasable monomer protein from non-neuronal cells that has activity-dependent neurotrophic activity for the survival of nerve cells, for example, spinal cord neurons, hippocampal neurons and cerebral cortical cultures. Furthermore, this protein plays a role in the prevention of neuronal cell death produced by the external envelope glycoprotein of the human immunodeficiency virus (HIV). This protein has been designated activity dependent neurotrophic factor (ADNF). The term "purified" as used herein refers to an electrophoretically pure protein as based on both isoelectric focusing gels and Tris tricine polyacrylamide gels.

The present inventors have isolated ADNF from non-neuronal rat cells (that is, rat glial cells), however, one skilled in the art can also isolate ADNF or homologous factors thereof from other species, including humans, without undue experimentation based on the present disclosure.

For example, ADNF could be isolated from human tissue by preparing human astroglial cultures from either fetal cerebral cortex or from adult brain at autopsy. Cultures would be treated with VIP as described hereinbelow. Biochemical isolation could then proceed as described for the rat tissue. In an alternative example, a human astrocyte cDNA library could be screened with either an oligonucleotide probe derived from the rat amino acid sequence of ADNF or rat cDNA for ADNF. Conservation between the rat gene and the human would allow hybridization to occur, thus permitting the isolation of cDNA for human ADNF and subsequent sequencing. With the cDNA known sequence, the library could be re-screened to obtain full length clones. The encoded protein could then be obtained from the full length cDNA using recombinant baculovirus or vaccinia virus expression systems (Sambrook et al., (1989)).

Figure 4:
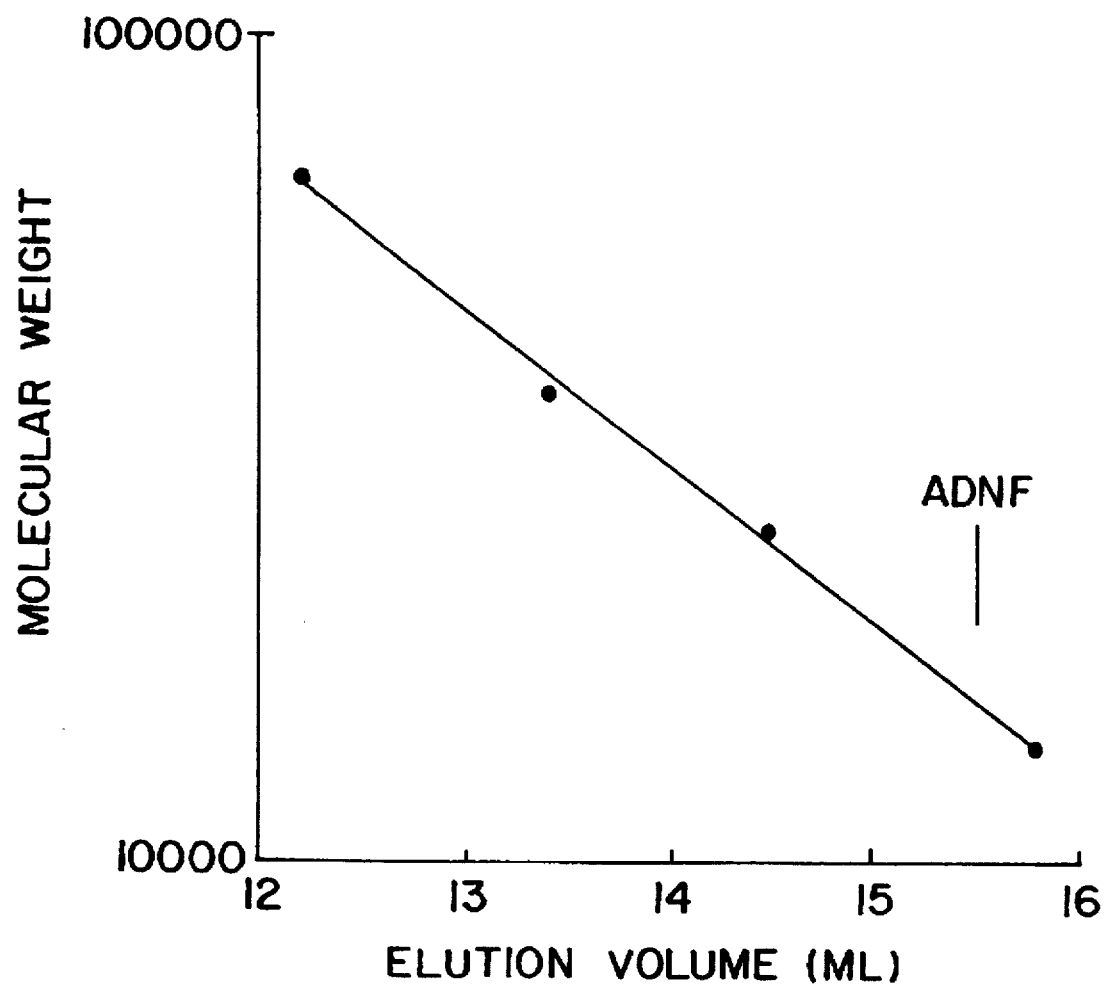
FIG. 4 represents molecular weight estimation from the gel permeation (sizing) chromatography. Samples from one FPLC size separation column are subjected to electrophoreseis through 2% Tris Tricine polyacrylamide gel (Analytical Biochem. 166: 368, 1987). A series of four molecular standards of known weight were used to calibrate the column. In the range from 67,000 (bovine serum albumin) to 13,700 (Ribonuclease A), the column separation as a function of elution volume was linear. Based on these separations and the observed elution volume of 15.5 ml for ADNF, the molecular weight is estimated to be 16,000 Daltons. The vertical line indicates the average elution volume for ADNF under these conditions. The other markers employed were ovalbumin (43,000) and Chymotrypsin (25,000).
Figure 7:
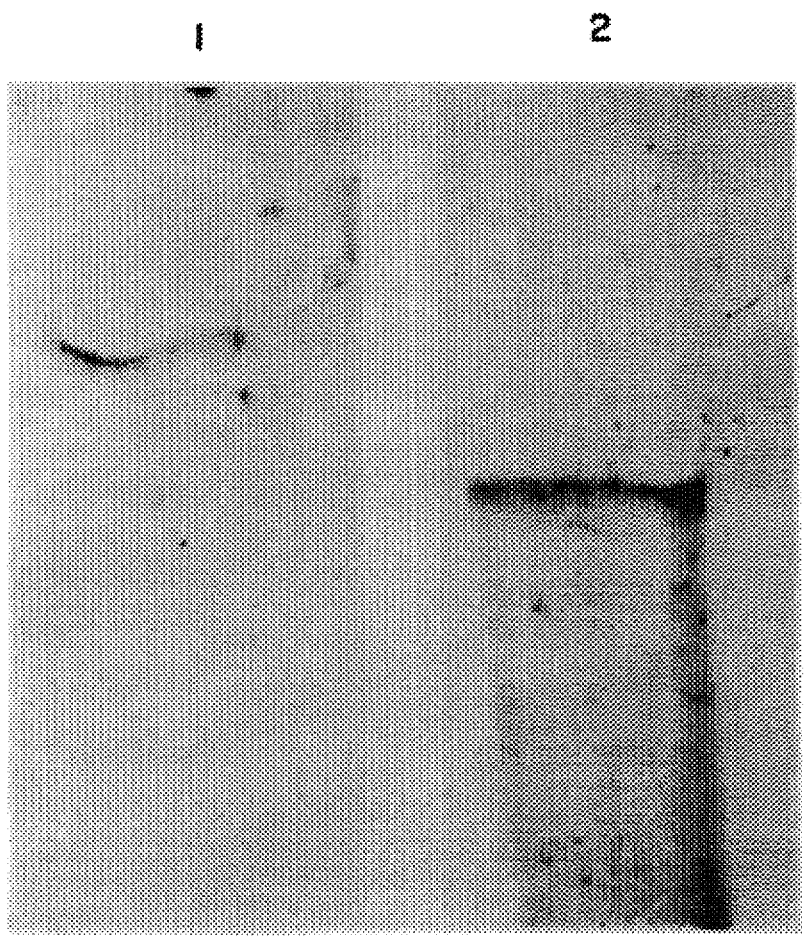
FIG. 7 demonstrates isoelectric focusing of the reverse phase FPLC purified neurotrophic activity. Samples from the reverse phase FPLC are subjected to isoelectric focusing (pH range 3.5–9.5), and silver stained. While fraction 31 from the size separation column (Lane 1) shows three basic protein bands, fraction 20 of the reverse phase (Lane 2) column displays only one protein exhibiting a pI of about 8.1.
Figure 8:
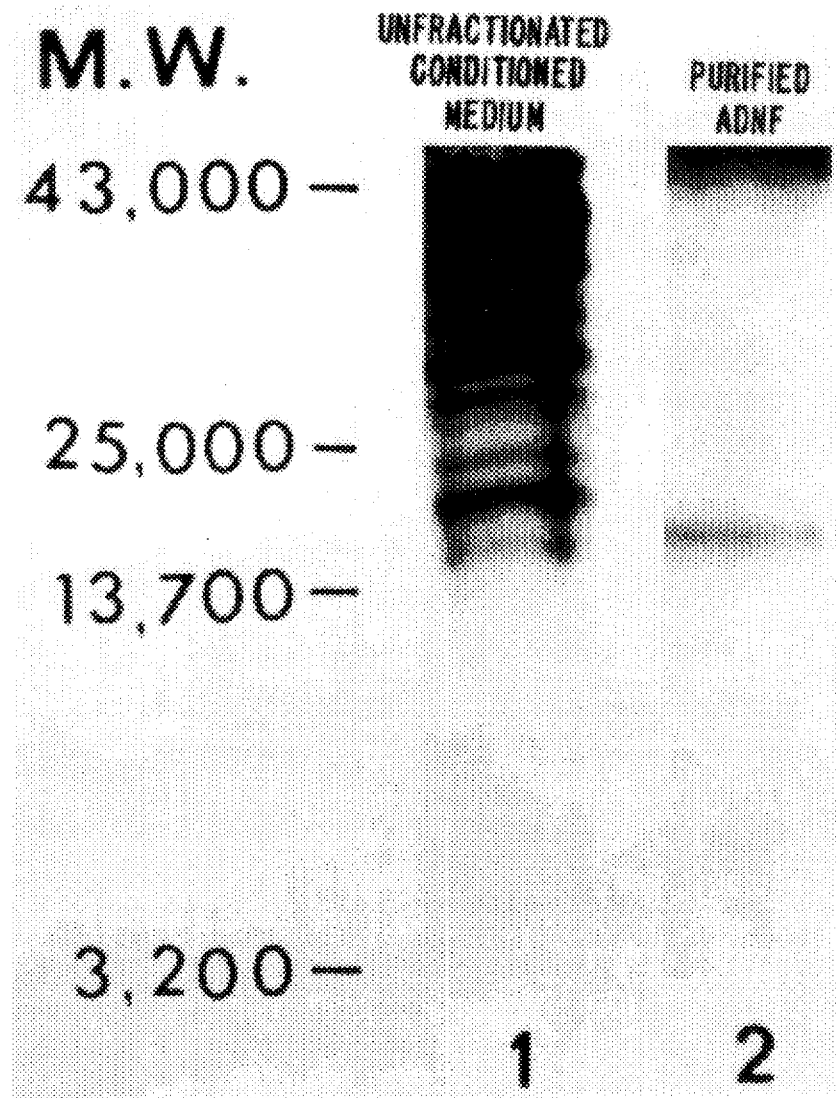
FIG. 8 represents Tris tricine polyacrylamide gel electrophoresis (Anal. Biochem 166, 368, (1987)) of intact conditioned medium (lane 1) and purified ADNF (lane 2) indicating an apparent molecular weight 18,500 Daltons for purified ADNF.

The purified ADNF has been structurally characterized as having a molecular weight of about 16,000 to 18,000 Daltons as determined by gel permeation chromatography (see FIG. 4) Tris tricine polyacrylamide gel electrophoresis (see FIG. 8), a basic pI of about 8.1 (see FIG. 7) and the amino acid composition given in Table I. ADNF is inactivated by trypsin and is heat-sensitive. As one skilled in the art will appreciate, the amino acid composition of purified ADNF may vary slightly due to allelic and species variations. The present invention also relates to peptide fragments of ADNF comprising at least 5 or 6 amino acids. Peptides that increase the survival of neuron cells may be used as an anti-HIV therapeutic agent.

The present invention further relates to DNA sequences encoding the ADNF protein of the present invention or fragments thereof which are at least 15 or 18 nucleotides in length. It is contemplated that probes could be designed based on the purified protein and utilized to obtain the cloned cDNA. Using recombinant methods, the DNA clone can be used to produce recombinant ADNF. Accordingly, the present invention also relates to DNA sequences encoding ADNF, to recombinant constructs including the DNA sequences and to host cells transformed therewith. Further, the invention relates to methods of using the transformed host cells to produce ADNF.

The present invention also relates, to antibodies specific for the purified ADNF protein or fragments thereof. Using standard methodology one skilled in the art can easily generate antibodies (monoclonal and/or polyclonal) to ADNF. For example, polyclonal antibodies can be elicited injecting test animals, such as rabbits, with the ADNF protein of the present invention and adjuvant. The animals are then bled and screened for the production of antibodies specific for the ADNF protein. Monoclonal antibodies specific for ADNF can be produced using known hybridization and screening techniques.

The purified ADNF of the present invention has been shown to protect neuronal cells against death. ADNF has the ability to increase the growth and survival of developing spinal cord neurons and cerebral cortical neurons. ADNF further protects neuronal cell viability by preventing neuronal cell death produced by the external envelope protein of the HIV virus.

Due to its ability to increase growth and survival of neurons, ADNF may have extensive use in the treatment of neurological deficiencies which result, for example, from neuronal development, aging, neurodegenerative diseases or spinal cord injury. Since the source of the protein is the cerebral cortex and the neuronal test system consists of cerebral cortical neurons as well as spinal cord neurons, it is likely that the ADNF protein has a broad spectrum of target neurons which respond to or require it for survival and/or growth. Preliminary studies suggest that blockade of vasoactive intestinal peptide (VIP) activity in vivo can result in morphological damage of nerve cells, impairment of acquisition of reflexes and loss of learning and memory mechanisms (Gozes et al., (1990) Soc. Neurosci. Abs. in press.; and Panililio et al., (1990) Soc. Neurosci. Abs. in press). Treatment with ADNF promoting neuronal cell growth and survival may elevate the damages resulting from VIP blockage and other neurological deficiencies.

Neurological deficiencies can be treated by administering to a patient the ADNF protein of the present invention or a biologically active fragment thereof, in an amount sufficient to promote survival or growth of neuronal cells.

The protein can be administered in the form of a pharmaceutical composition comprising the purified protein or a derivative of ADNF, such as, a D-Ala derivative, and a pharmaceutically acceptable carrier. The protein is present in the composition in an amount sufficient to promote survival or growth of neuronal cells when the composition is administered to a patient.

The protein can be administered into the spinal fluid. Alternatively, the protein can be administered intravenously or intranasally in a lipophilic form. For example, the protein can be administered in a lipophic emulsion carrier. The protein may also be modified to increases its lipophilicity.

In addition, studies conducted with developing hippocampal neurons grown in cell culture have indicated that ADNF can prevent neuronal cell death associated with the external envelope protein of the HIV virus, the causative agent of AIDS. Thus, the protein of the present invention can be used as a therapeutic agent in the treatment of AIDS.

Neuronal cell death in patients infected with an HIV virus may be prevented by administering to that patient the purified protein of the present invention or a biologically active fragment thereof, in an amount sufficient to prevent cell death and a pharmaceutically acceptable carrier. The amount of ADNF to be administered will depend on the route of administration utilized and on the patient's condition but can be easily determined by the patient's physician.

The following non-limiting examples are provided to aid in the understanding of the present invention, the true scope of which is set forth in the appended claims. It is understood that modifications can be made in the procedure set forth, without departing from the true spirit of the invention.

EXAMPLES

Techniques of Isolation and Detection:

To isolate activity dependent factors, two different cell cultures were used. The source of the neurotrophic factors was rat cortical astrocytes prepared according to previously described methods (McCarthy, K. D. and Partlow, L. M. (1976) Brain Res. 114, 391–414; and Evans et al., (1984) J. Neurochem. 43, 131–138). Three and a half week old cultures (confluent 75 cm$^2$ flasks) were washed three times with phosphate buffered saline (PBS) and conditioned medium was collected (10 ml/flask) during a 3 hour incubation with 0.1 nM VIP. The medium was then centrifuged (3000×g for 10 min) and dialyzed (10 kDalton cutoff) against 50 mM sodium phosphate buffer, pH 7.0.

The second type of cell culture, mouse spinal cord cultures, were used to test for biological activity of the conditioned medium. Dissociated mouse spinal cord cultures (obtained from 12-day-old embryos) were plated (0.5 million cells/35 mm dish) in medium consisting of 10% fetal calf serum and 10% heat inactivated horse serum in minimum essential medium (MEM). After 24 hours, the medium was changed to 5% horse serum in MEM supplemented with defined medium components (Romijn et al., (1982) Dev. Brain Res. 2, 583–589). After nine days in vitro, the cultures were given a complete change of medium and treated with 1 µM tetrodotoxin and varying concentrations of fractionated conditioned medium for five days. Neuronal cell counts were conducted after immunocytochemical identification with antisera against neuron specific enolase (Levi-Montalcini, R. and Angeletti, P. V. (1968) Physiol. Rev. 48, 534–569). Counts were made in 30 fields from predetermined coordinate locations without knowledge of the treatment group.

Figure 1:
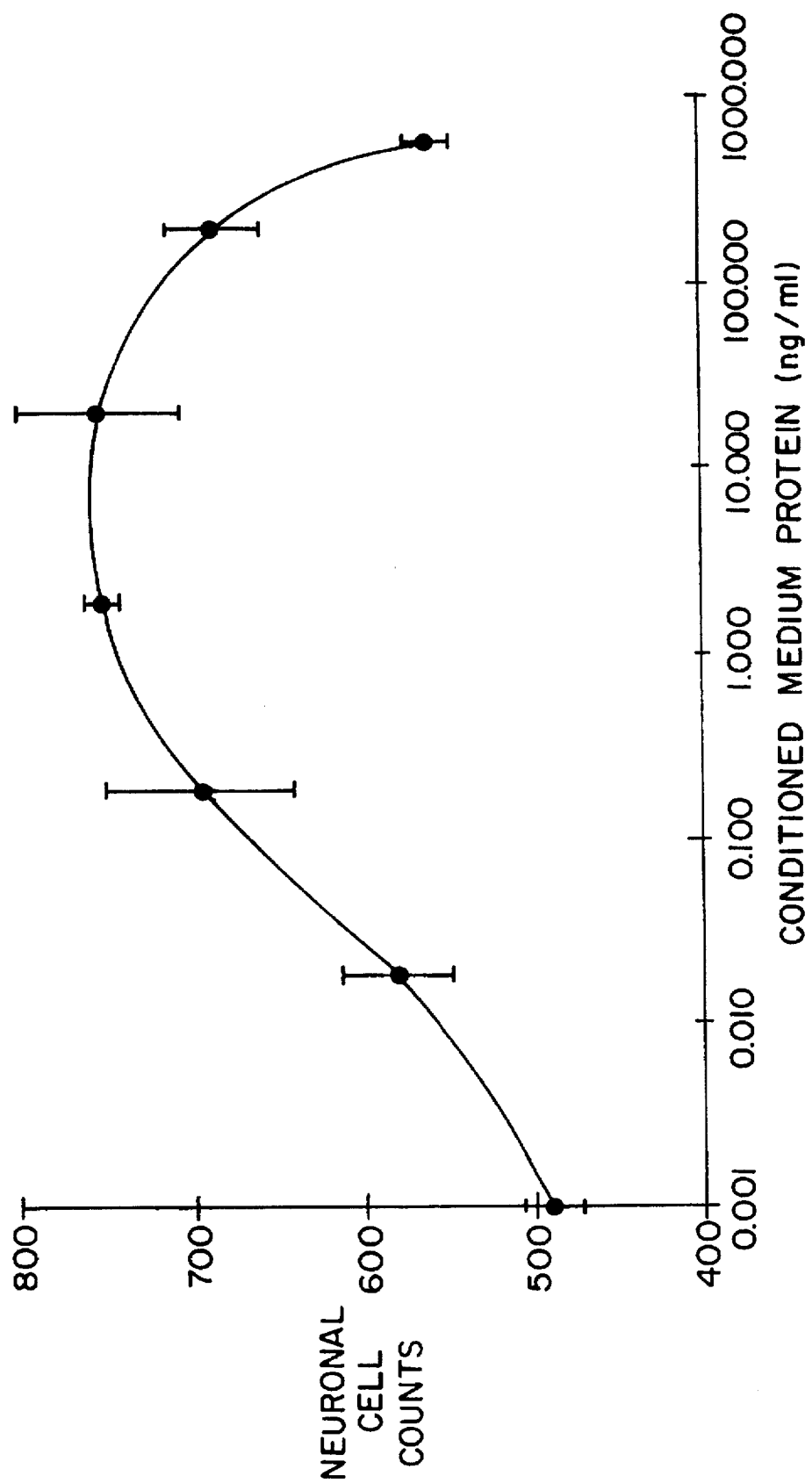
FIG. 1 demonstrates the survival-promoting activity in unfractionated conditioned medium from astroglial cultures: effect on spinal cord neurons. Spinal cord test cultures were treated for five days with varying amounts of conditioned medium. All test cultures were co-treated with 1 μM tetrodotoxin to block electric activity and inhibit the release of vasoactive intestinal peptide. Treatment was started on day 9 in vitro. Each value is the mean±SEM of 3 determinations.

The concentration-dependence effects of unfractionated, dialyzed conditioned medium on neuronal survival is shown in FIG. 1.

The survival factor (ADNF) is inactivate by trypsin and is also heat-sensitive.

Figure 2:
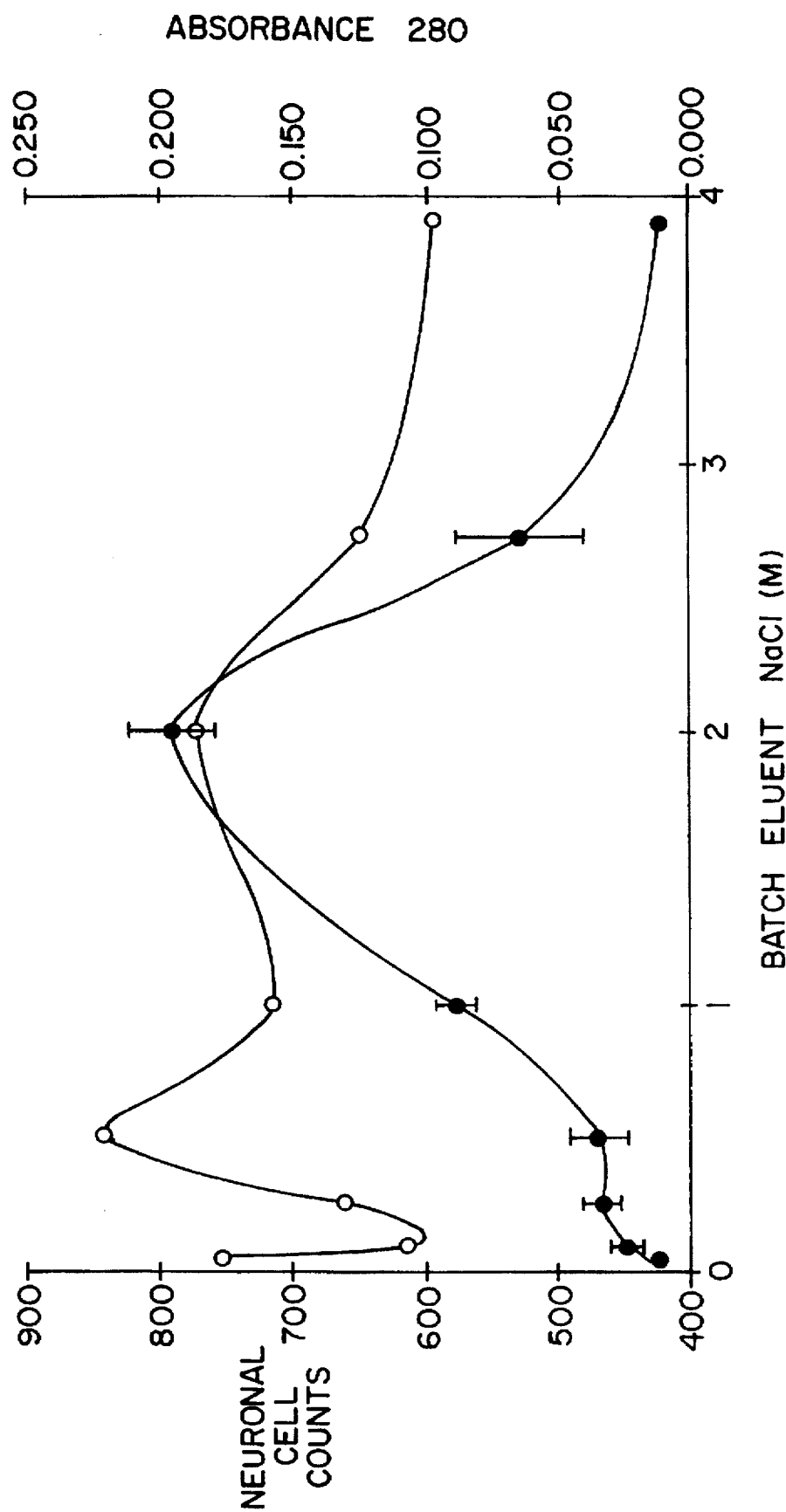
FIG. 2 shows the identification of the neurotrophic fraction eluted by increasing salt concentrations from DEAE-ion exchange column (closed circles). Each value is the mean of 3 determinations±SEM. A 5-day test period is begun nine days after plating of the embryonic SC/DRG tissue. Column fractions (1:10,000) are added together with 1 μM tetrodotoxin. Significant increases in neuronal cell counts are observed in the 2M NaCl eluate. Open circles represent O.D. 280 absorbance of each fraction.

The dialyzed material was then loaded onto a DEAE SEPHACEL, diethylaminoethyl sephacel, (Pharmacia AB Biotechnology, Uppsala, Sweden) column (0.75 cm diameter and 3 cm length) pre-equilibrated with 50 mM sodium pyro-phosphate buffer, pH 7.0. About 300 ml of dialyzed material (1–2 mg of protein) was loaded onto the column, and washed sequentially with 40 ml of 50 mM sodium pyro-phosphate buffer (pH 7.0) and then the same buffer supplemented with increasing concentrations of NaCl: 0.1M, 0.26M, 0.5M, 1.0M, 2M and 3M. Fractions were extensively dialyzed against deionized water (at 4° C.) and tested at two dilutions: 1:10,000 and 1:100,000. Maximal biological activity was discovered at the 2M NaCl fraction (FIG. 2). This fraction was thereafter used for further purification.

Figure 3:
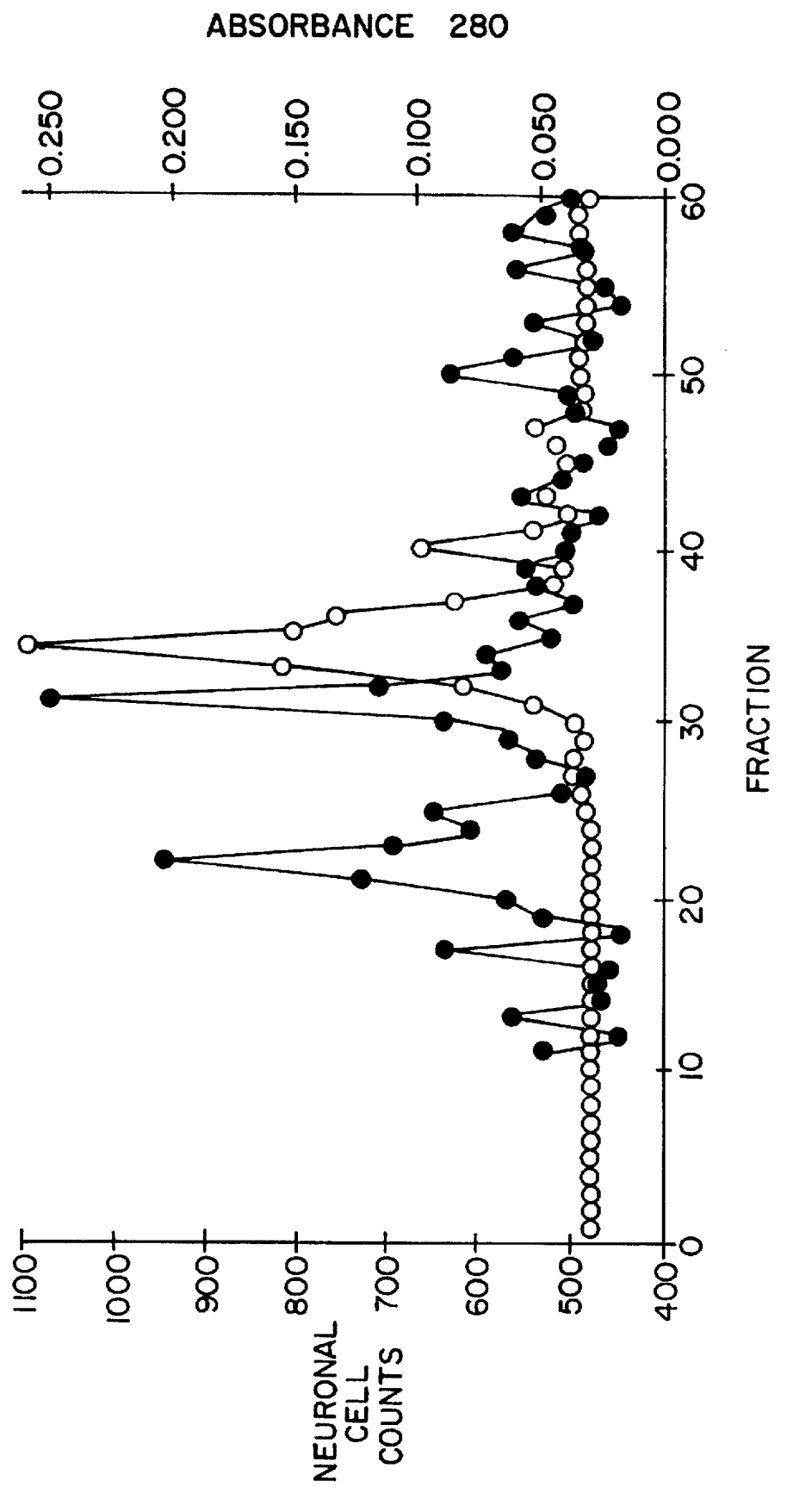
FIG. 3 shows size separation of the DEAE (2M NaCl eluate) activity-dependent neurotrophic fraction by gel permeation chromatography (closed circles). A 5-day test period is started nine days after plating of the embryonic SC/DRG tissue. Column fractions (1:10,000) are added together with 1 μM tetrodotoxin. Significant increases in neuronal cell counts are observed in column fractions 22 and 31. Open circles represents O.D. 280 absorbance of each fraction.

Following the ion exchange chromatography, the 2M NaCl fraction was further purified using gel permeation chromatography. For size separation, a SUPEROSE™ 12 (pre-packed HR 10/30) column in fast performance liquid chromatography (FPLC system, Pharmacia) was used. The DEAE SEPHACEL®, diethylaminoethyl sephacel, (Pharmacia AD Biotechnology, Uppsala, Sweden) eluate at 2M NaCl was dialyzed extensively against deionized water, lyophilized and resuspended in 0.5 ml of 50 mM sodium phosphate (pH 7.3) containing 0.15M NaCl. 0.25 ml aliquots (corresponds to 150 ml of original material) were loaded onto the column. Fractions (0.5 ml) were collected from the column. Two peaks of activity were discovered, one at fraction 22 and another at fraction 31 (fractions were tested at 1:10,000 dilutions). The estimated molecular weights of fraction 22 was 150,000 Daltons and of fraction 31 was 16,000 Daltons (see FIG. 3 and FIG. 4).

Identification of Novel Activity-Dependent Neurotrophic Factor (ADNF):

The activity-dependent factors, isolated and characterized as described above, were subjected to analysis of size and structure.

Fractions 22 and 31 obtained as described above were dialyzed extensively against deionized water, lyophilized, filtered and subjected to Tris tricine polyacrylamide gel electrophoresis (Anal. Biochem. 166: 368, 1987). Purified ADNF resulted in one band, migrating at about 18,500 Daltons (see FIG. 8).

Figure 5:
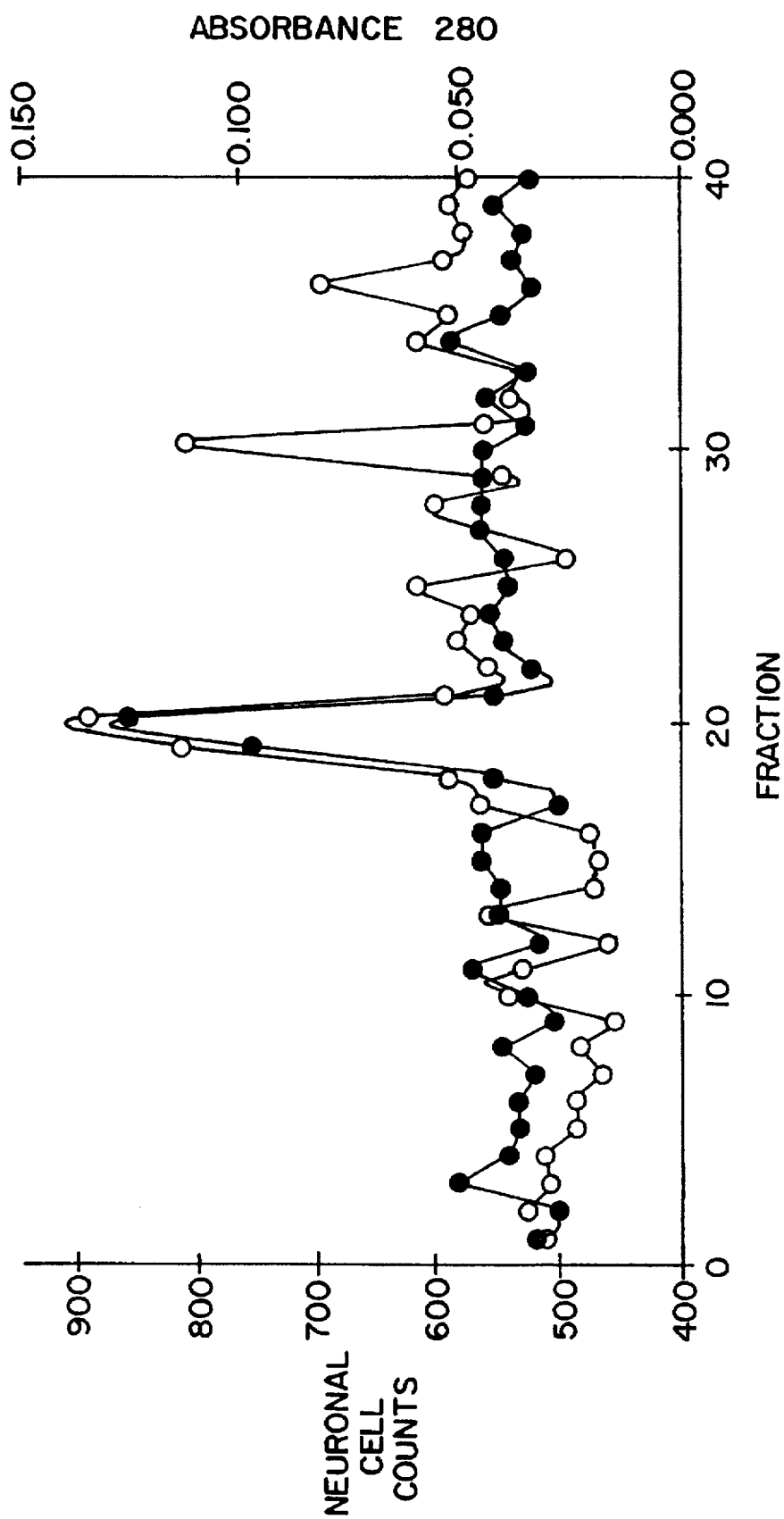
FIG. 5 shows purification of the low molecular weight neurotrophic activity by hydrophobic interaction chromatography (Closed circles). The same experiment as in FIGS. 1 and 2 is performed. Results shown indicate that fraction 20 contains the neurotrophic activity. Open circles represent O.D. 280 absorbance of each fraction.

To purify further the protein associated with biological activity, fraction 31 of the sizing-FPLC column, hydrophobic interaction-FPLC (Alkyl SUPEROSE™ HR5/5, Pharmacia AB Biotechnology, Uppsala, Sweden) was used. The sample (fraction 31, 0.5 ml) was dialyzed extensively against deionized water and lyophilized. It was thereafter resuspended in water and diluted with a buffer to a final concentration of 0.1M sodium phosphate buffer, pH 7.0 containing 1.43M $(NH_4)_2SO_4$. Prior to loading, the column was washed with 0.1M phosphate buffer (pH 7.0) and then equilibrated with 0.1M phosphate buffer (pH 7.0) containing 2.0M $(NH_4)_2SO_4$. Elution was performed with a linear gradient of salt removal (2.0–0.0M) over 25 min. Samples were tested for biological function, using the spinal cord cell culture system, as described above. Results shown in FIG. 5 demonstrate that the neuronal survival activity was concentrated fraction 20.

Isoelectric focusing was performed using LKB ampholine gel plates (pH range 3.5–9.5, Pharmacia) and electrophoresis was carried out for 3 hours in a flat bed apparatus (multiphor, Pharmacia), voltage set: 1500 Volts, amperage set: 50 mA. Gels were stained with silver stain (BioRad). Results showed three protein bands in fraction 31 (sizing column-FPLC) and one protein band in fraction 20 of the reverse phase (hydrophobic interaction) column. All protein bands are of basic nature (see FIG. 7), the approximate pI of the protein band in fraction 20 was 8.1

In addition, the purified growth factor was analyzed for its total amino acid composition. In 0.84 μg of purified material, the amino acid composition given below in Table I was observed.

TABLE I

| Amino Acid | Residues/mol |
|---|---|
| Asx | 19 |
| Thr | 6 |
| Ser | 18 |
| Glx | 28 |
| Pro | 8 |
| Gly | 41 |
| Ala | 12 |
| Val | 10 |
| Met | 2 |
| Iso | 8 |
| Leu | 14 |
| Tyr | 4 |
| Phe | 6 |
| His | 3 |
| Trp | ND |
| Lys | 8 |
| Arg | 8 |
| Cys | ND |

Partial sequence analysis of ANDF was obtained by V8-protease digests as previously described (Proc. Natl. Acad. Sci. USA 82: 6507–6511, (1985)) and the peptides were separated on a HPLC by reverse phase chromatography. The following fragments were obtained:

Fragment I -Xaa-Xaa-Xaa-Gln-Pro-Xaa-Thr-Lys-Asn-Gly (SEQ ID NO:1).

Fragment II -Leu-Xaa-Xaa-Xaa-Ser-Ala-Leu-Arg-Ser-Ile-Pro-Ala-Leu (SEQ ID NO:2)

Fragment III -Pro-Ala-Leu-Asp-Ser-Leu-Lys-Pro-Ala-Asn-Glu-(SEQ ID NO:3) wherein Xaa refers to an unknown amino acid.

Figure 9:
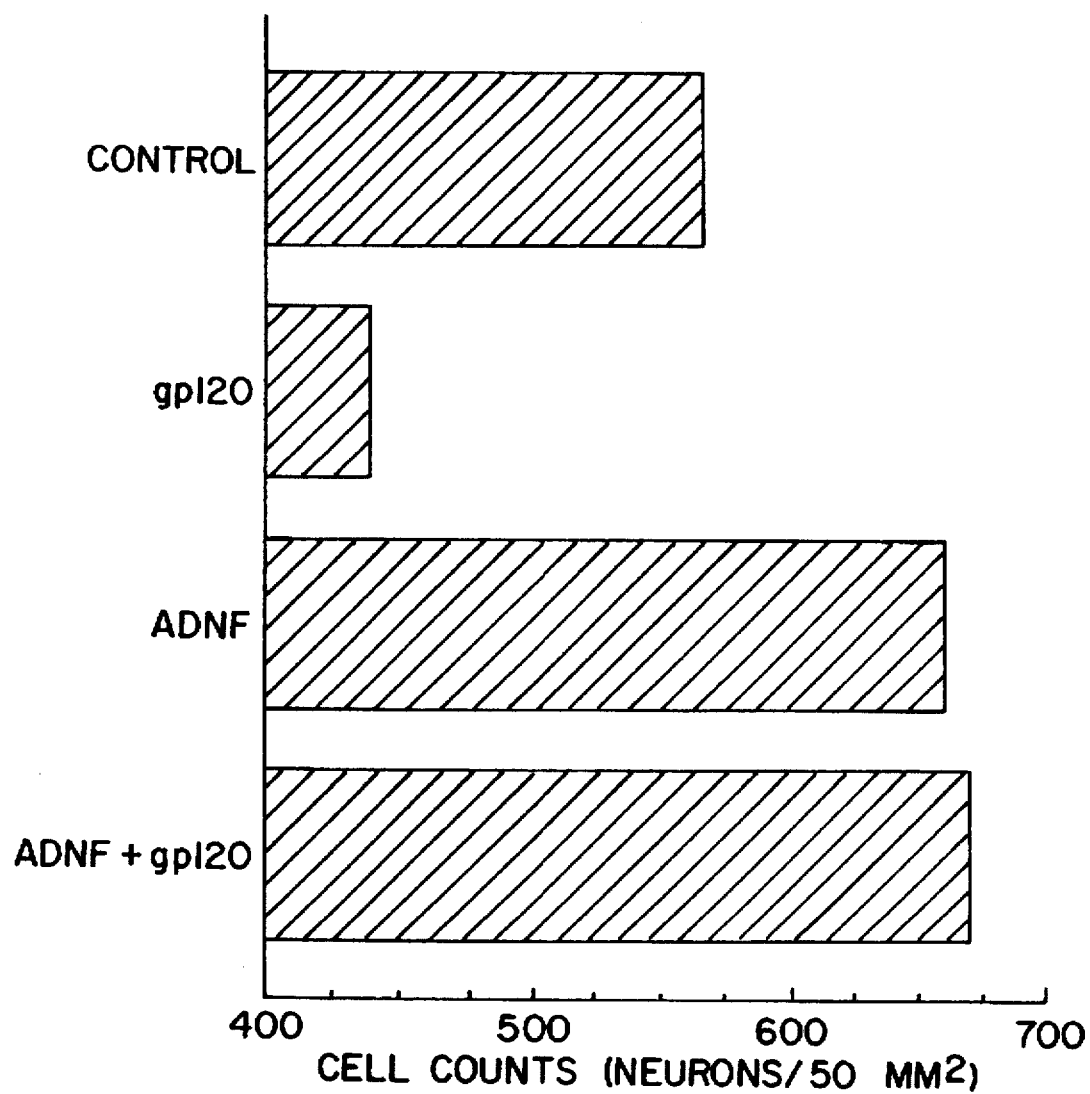
FIG. 9 demonstrates the ability of ADNF to prevent neuronal cell death associated with human immunodeficiency virus (HIV) external envelope glycoprotein. Murine hippocampal cultures were treated for 5 days with 1 pM gp120 (strain: RF II). Cells were counted by image analysis and confirmed by visual examination.

Identification of Activity of ADNF:

Developing hippocampal neurons were grown in cell culture as previously described (Forsythe and Westbrook, (1988) J. Physiol. London 396, 515–533). The cultured cells were treated with 1 pM ADNF and subjected to 1 pM gp120 (strain: RF II). Cells were counted by image analysis and confirmed by visual examination. The results are shown in FIG. 9.

To test ADNF for anti-gp120 activity previously employed methods were used (Brenneman et al., (1988) Drug Dev. Res. 15, 361–369). Briefly, one week old hippocampal cultures (Forsythe and Westbrook (1988) J. Physiol. Lond. 396, 515–533), were incubated for 5 days with 1 pM gp120 (strain: RF II). Cultures were then fixed in glutaraldehyde, counted by image analysis and observations confirmed by visual examination. As the test agent 1 pM of ADNF was used. The ADNF was added in a vehicle consisting of phosphate buffered saline containing 0.01% bovine serum albumin.

Figure 10:
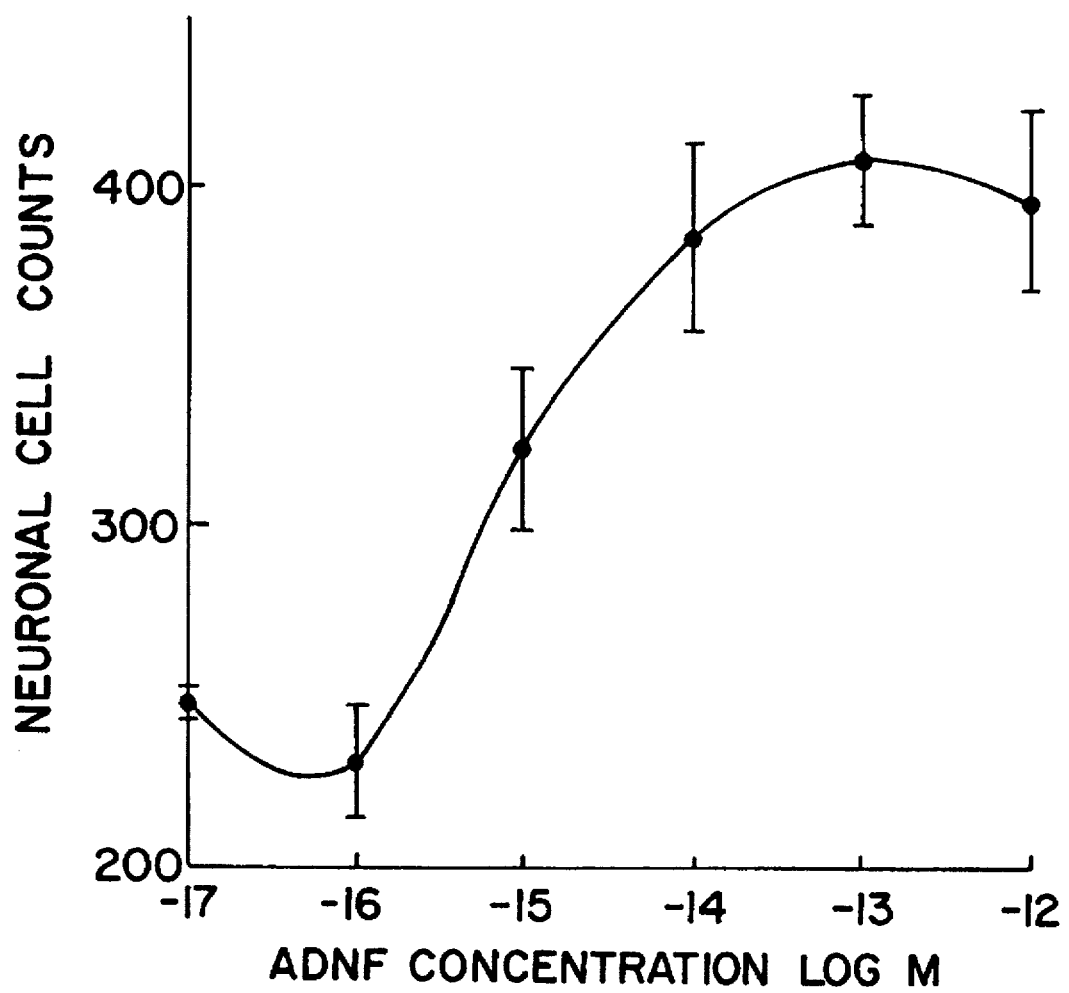
FIG. 10 demonstrates that ADNF prevents tetrodotoxin-induced death in cerebral cortical cultures in a dose responsive manner. Purified ADNF was added to cultures 9 days after plating the neurons. The duration of the experiments was 5 days, with only one treatment of ADNF given at the beginning of the test period. To block electrical activity, 1 μM tetrodotoxin was given. Each value is the mean of three determinations±SEM.
Figure 11:
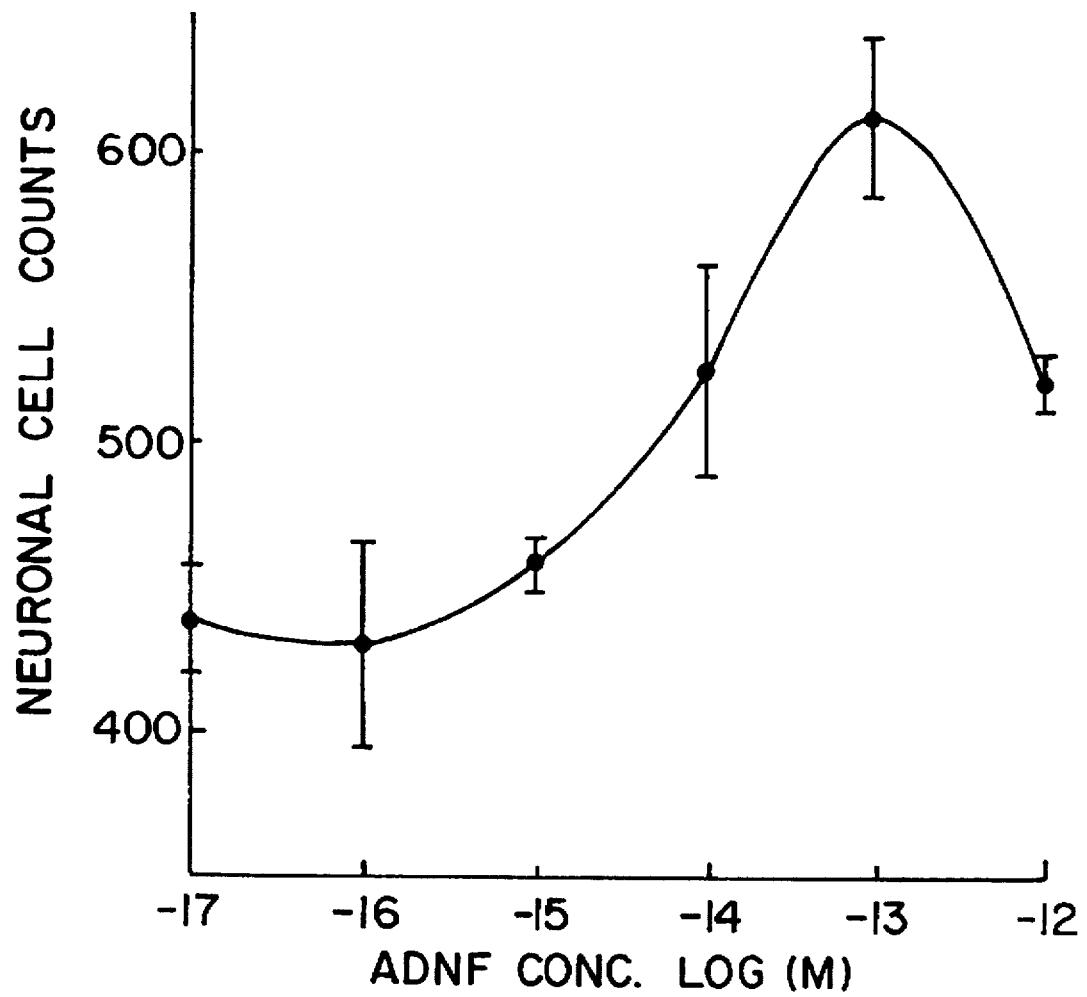
FIG. 11 demonstrates that ADNF can increase the survival of developing cerebral cortical neurons in cell culture. The same, assay was performed as was described in FIG. 10, except that no tetrodotoxin was added.

To further test the ability of purified ADNF to increase the survival of developing neurons, another cell type was chosen, cerebral cortical neurons. Cerebral cortical cultures were prepared by a slight modification of the techniques described by Forsythe and Westbrook, 1988; the cerebral cortex was utilized instead of hippocampus and new born rats were used instead of E16 mice. For the assay, purified ADNF was added to cultures 9 days after plating. One treatment of ADNF was given at the beginning of the five-day test period. Survival of cells which have been treated with or without 1 uM tetrodoxin are shown in FIGS. 10 and 11 respectively.

Figure 12:
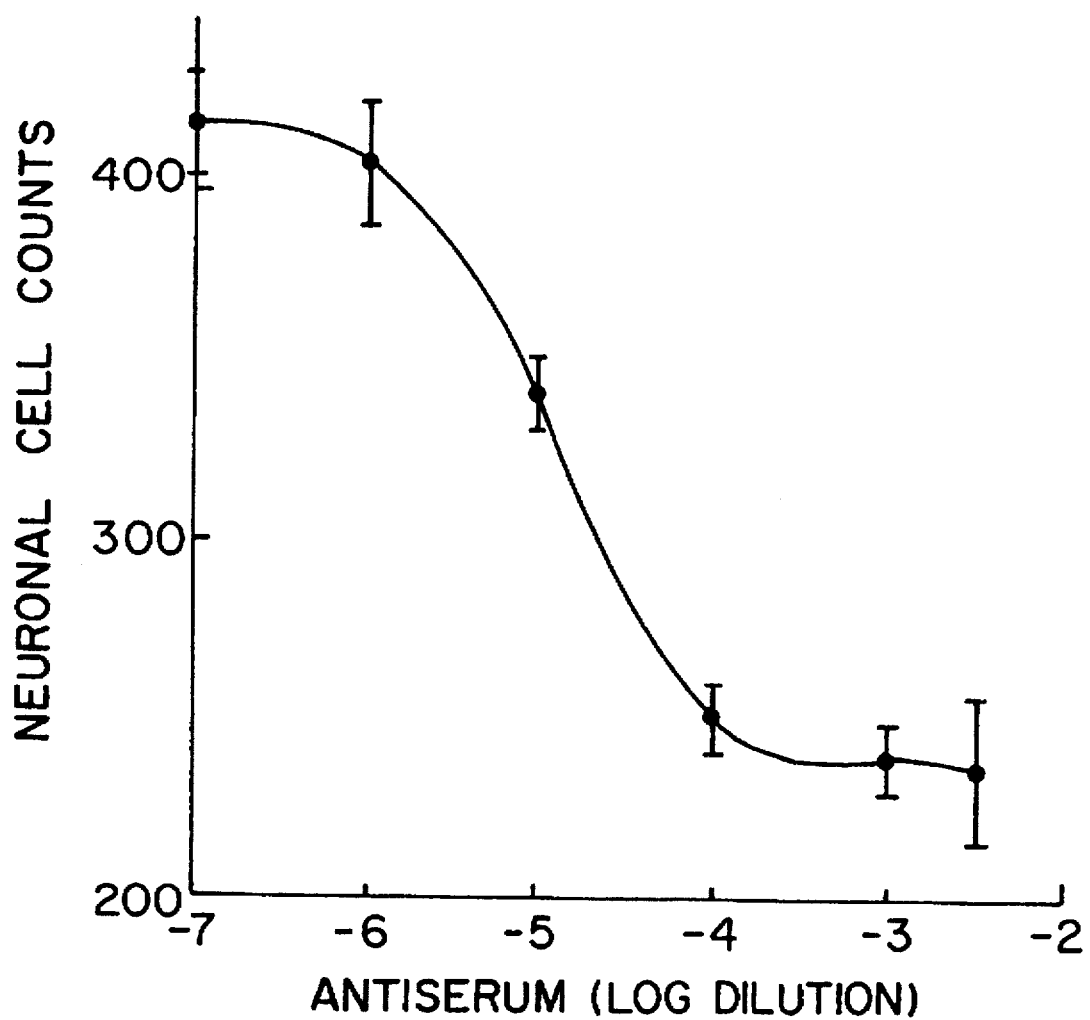
FIG. 12 demonstrates the effect of antiserum to ADNF on survival of cerebral cortical neurons. Neutralizing antiserum was obtained by serial injections of purified ADNF into mice. As shown, the anti-ADNF produced neuronal cell death in cerebral cortical cultures.

Effect of antiserum to ADNF on neuronal survival of cerebral cortical neurons:

Neutralizing antiserum was obtained by serial injections of purified ADNF into mice. As shown in FIG. 12, the anti-ADNF produced neuronal cell death in cerebral cortical cultures. The antibody-induced cell death could be prevented by co-administration of ADNF. Control anti-serum produced no neuronal cell death at the same dilutions employed with the ADNF.

All publications mentioned hereinabove are hereby incorporated by reference.

While the foregoing invention has been described in some detail for purposes of clarity and understanding, it will be appreciated by one skilled in the art from a reading of this disclosure that various changes in form and detail can be made without departing from the true scope of the invention.

What is claimed is:

1. A purified non-neuronal activity dependent neurotrophic factor (ADNF) protein derivable from a glial cell that increases the survival of neuron cells, said ADNF protein having a basic pI of about 8.1 as determined by isoelectric focusing and a molecular weight of 16,000 to 18,000 Daltons as determined by tris tricine polyacrylamide gel electrophoresis and fast performance liquid chromatography (FPLC).

2. The purified protein according to claim 1 wherein the neuron cells are spinal cord neuron cells or hippocampal neuron cells or cerebral cortical neuron cells.

3. The purified protein according to claim 1 having the amino acid composition given in Table I.

4. The purified protein according to claim 1 wherein said protein is derivable from rodent glial cells.

5. The purified protein according to claim 1 wherein said protein is derivable from human glial cells.

6. An antibody which specifically binds the purified protein according to claim 1.

7. The antibody according to claim 6 which is monoclonal.

8. The antibody according to claim 6 which is polyclonal.

9. A purified non-neuronal ADNF protein produced by a process comprising the steps of:

i) culturing glial cells producing neurotrophic factors;

ii) collecting culture medium from said cells;

iii) fractionating components of said medium by ion exchange chromatography;

iv) assaying the fractions resulting from step (iii) for the ability to increase in vitro neuronal survival, wherein maximal ADNF biological activity is found in the 2M NaCl fraction;

v) subjecting fractions from step (iv) found to possess said activity to gel permeation chromatography;

vi) assaying the fractions resulting from step (v) for the ability to increase in vitro neuronal survival; and vii) collecting active fractions from step (vi) wherein said non-neuronal ADNF protein has a basic pI of about 8.1 as determined by isoelectric focusing and a molecular weight of 16,000 to 18,000 Daltons as determined by tris tricine polyacrylamide gel electrophoresis and fast performance liquid chromatography (FPLC).

10. The purified protein according to claim 1 wherein the primary amino acid sequence of said protein comprises peptide fragments consisting essentially of the following amino acid sequences:

-Xaa-Xaa-Xaa-Gln-Pro-Xaa-Thr-Lys-Asn-Gly (SEQ ID NO: 1);

-Leu-Xaa-Xaa-Xaa-Ser-Ala-Leu-Arg-Ser-Ile-Pro-Ala-Leu (SEQ ID NO:2)

-Pro-Ala-Leu-Asp-Ser-Leu-Lys-Pro-Ala-Asn-Glu (SEQ ID NO:3) wherein Xaa refers to an unknown amino acid.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: one-of(1, 2, 3, 6)
        ( D ) OTHER INFORMATION: /product="Xaa = unsure amino acid"

(x i) SEQUENCE DESCRIPTION: SEQ ID NO:1:

```
Xaa Xaa Xaa Gln Pro Xaa Thr Lys Asn Gly
1               5                   10
```

(2) INFORMATION FOR SEQ ID NO:2:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: one-of(2, 3, 4)
        (D) OTHER INFORMATION: /product="Xaa = unsure amino acid"

(xi) SEQUENCE DESCRIPTION: SEQ ID NO:2:

```
Leu Xaa Xaa Xaa Ser Ala Leu Leu Arg Ser Ile Pro Ala Leu
1               5                   10
```

(2) INFORMATION FOR SEQ ID NO:3:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

```
Pro Ala Leu Asp Ser Leu Lys Pro Ala Asn Gly
1               5                   10
```